US008366777B2

(12) United States Patent
Matthis et al.

(10) Patent No.: US 8,366,777 B2
(45) Date of Patent: Feb. 5, 2013

(54) EXPANDABLE INTERVERTEBRAL IMPLANT

(75) Inventors: Wilfried Matthis, Weisweil (DE); Lutz Biedermann, VS-Villingen (DE); Jürgen Harms, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 1444 days.

(21) Appl. No.: 11/944,580

(22) Filed: Nov. 23, 2007

(65) Prior Publication Data
US 2008/0147193 A1    Jun. 19, 2008

Related U.S. Application Data

(60) Provisional application No. 60/860,944, filed on Nov. 24, 2006.

(30) Foreign Application Priority Data

Nov. 23, 2006  (EP) .................................... 06024332

(51) Int. Cl.
*A61F 2/44*    (2006.01)
(52) U.S. Cl. .................................. 623/17.16; 623/17.11
(58) Field of Classification Search ............... 623/17.11, 623/17.15–17.16
See application file for complete search history.

(56) References Cited

U.S. PATENT DOCUMENTS

| 5,658,335 | A  |   | 8/1997 | Allen |
| 6,176,882 | B1 |   | 1/2001 | Biedermann et al. |
| 6,530,936 | B1 | * | 3/2003 | Yun ............................... 606/167 |
| 2005/0125062 | A1 |   | 6/2005 | Biedermann et al. |
| 2006/0241770 | A1 | * | 10/2006 | Rhoda et al. ............... 623/17.15 |
| 2006/0253201 | A1 |   | 11/2006 | McLuen |
| 2007/0255415 | A1 | * | 11/2007 | Edie et al. .................. 623/17.16 |

FOREIGN PATENT DOCUMENTS

| WO | WO 99/42062 |    | 8/1999 |
| WO | WO 02/09626 | A1 | 2/2002 |
| WO | WO 2004/080356 | A2 | 9/2004 |
| WO | WO 2005/058209 | A2 | 6/2005 |

OTHER PUBLICATIONS

European search report dated Apr. 26, 2007 for EPO Application No. 06024332.6, European Search Report mailed May 15, 2007; Biedermann Motech GmbH (8 pp.).

* cited by examiner

*Primary Examiner* — Andrew Yang
*Assistant Examiner* — Olivia C Chang
(74) *Attorney, Agent, or Firm* — Christie, Parker & Hale, LLP

(57)  ABSTRACT

An expandable intervertebral implant includes a front wall, a back wall spaced apart from the front wall, and two side walls connecting the front wall and the back wall at their respective ends. The walls define a space. The implant further includes a bottom face, a top face, at least one engagement member with an engagement surface for engagement with the end plate of a vertebral body, a first adjusting element and a second adjusting element which are supported by a first support member and a second support member, respectively, and which cooperate with the respective support member such that the engagement member is reciprocally movable between a first end position and a second end position. In the first end position, the engagement surface does not project beyond the bottom face or the top face and in the second end position, the engagement surface at least partially projects outwardly beyond the bottom face or the top face. The first and the second support members are coupled by a coupling mechanism.

20 Claims, 9 Drawing Sheets

EXPANDABLE INTERVERTEBRAL IMPLANT

CROSS-REFERENCE TO RELATED APPLICATION(S)

The present application claims the benefit of U.S. Provisional Patent Application Ser. No. 60/860,944, filed Nov. 24, 2006, and claims priority from European Patent Application EP06024332.6, filed Nov. 23, 2006, the entire disclosures of which are incorporated herein by reference.

BACKGROUND

The present application generally relates to intervertebral implants, and more particularly, to an expandable intervertebral implant.

An intervertebral implant is inserted after removal of an intervertebral disk for stabilizing the intervertebral region until bone material which is filled in at the same time has grown to an osseous connection and strengthening.

An expandable intervertebral implant is known from U.S. Pat. No. 6,176,882 B1. The intervertebral implant comprises two spaced side walls, a front wall connecting the side walls at one end thereof, a back wall connecting the side walls at the other end, the walls defining a corresponding space within the walls, a bottom face, a top face, each face extending transversely to said walls, at least one engagement member disposed within the space defined by said walls, said engagement member having a surface oriented toward one of the bottom face or the top face, and two wedge members which are supported in the front wall and the back wall by a threaded spindle having two ends and two portions with opposite thread pitches, one end of the threaded spindle being rotationally supported in the front wall and the other end being rotationally supported in the back wall. The two wedge members are supported within the space in such a manner that, upon rotation of the threaded spindle in one direction, a distance between the wedge members decreases and, upon rotation of the threaded spindle in an opposite direction, the distance between the wedge members increases. The wedge members operate to move the engagement member reciprocally. The outer contour of the expandable intervertebral implant is rectangular. Therefore, the wedge members can be supported on one single threaded spindle.

Another expandable intervertebral implant is known, for example, from WO 2005/058209 A2. The implant includes a body having a longitudinal axis and including first and second axial walls spaced apart along a transverse axis, first and second transverse end walls extending between and interconnecting the first and second axial walls. The intervertebral implant includes an expansion member co-acting with the axial walls to expand the body along the transverse axis. The outer contour of the implant in a plane parallel to the end plates of the vertebral body is also rectangular. An intervertebral implant with a rectangular contour does not fit perfectly to the shape of the end plates of the vertebral body. For certain applications an anatomically-shaped intervertebral implant is desired.

US 2005/0125062 discloses a height adjustable intervertebral implant which has an anatomical shape.

Based on the above, there is a need to provide an expandable intervertebral implant which allows a facilitated insertion and at the same time has an improved simple handling of the expansion mechanism.

SUMMARY

The disclosure relates to an expandable intervertebral implant comprising a front wall, a back wall and a two side walls connecting the front wall and the back wall, the walls defining a cavity having an open bottom and top, and at least one member movable in the cavity from a first position wherein its surface does not project out of the cavity and a second position wherein its surface at least partially projects out of the cavity. The implant is actively expandable from either of two sides. Further, the implant has an anatomical shape.

The intervertebral implant is anatomically-shaped, in particular, it has a banana-shape or a kidney-shape. However, due to the expansion mechanism of the intervertebral implant according to the invention, it can be easily adapted to have any other shape which is even more adapted to the natural shape of the end plate of the vertebral bodies.

The intervertebral implant can be expanded by accessing it from either side.

Various coupling mechanisms can be used to couple the rotational motion of one support member which serve for expanding the implant to the other support member.

Further features and advantages of the invention will become apparent and will be best understood by reference to the following detailed description of embodiments taken in conjunction with the accompanying drawings.

DETAILED DESCRIPTION OF THE DRAWINGS

DETAILED DESCRIPTION

Figure 1:
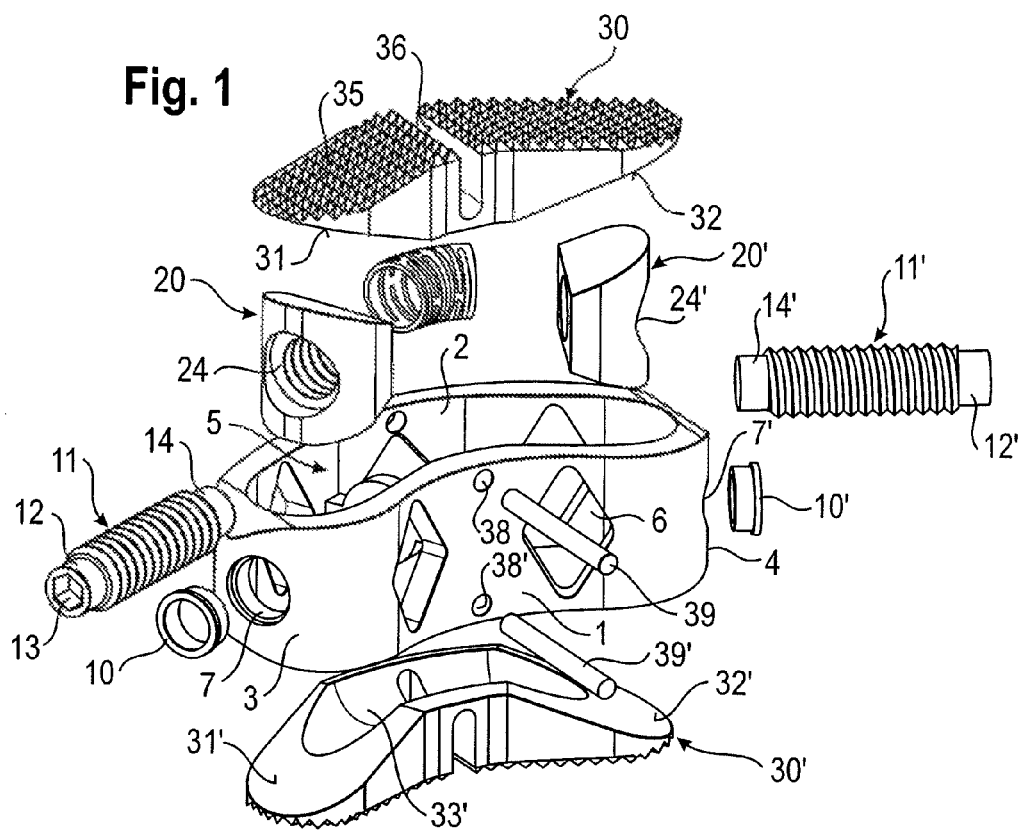
FIG. 1 shows an exploded perspective view of the intervertebral implant according to a first embodiment.

As shown in FIGS. 1 to 7, the expandable intervertebral implant includes a front wall 1, a back wall 2 spaced apart from the front wall, and first side wall 3 connecting the front wall 1 and the back wall 2 at their one end as well as a second side wall 4 opposite to the first side wall for connecting the front wall and the back wall at their opposite other ends. As best shown in FIG. 1, the bottom and top faces are open so that the four walls define a cavity 5 having an open bottom and an open top. The front wall 1 and the back wall 2 have approximately the same length and are curved in approximately the same direction. The side walls 3 and 4 are shorter and connect the front wall 1 and the back wall 2 in such a way that a substantially banana-shaped or kidney-shaped contour is defined by the walls. The length and the curvature of the respective front and back wall and the side walls can be selected so as to be adapted to the size and shape of the opposing end plates of the vertebral bodies between which the implant is to be inserted. The height of the front wall 1 and the back wall 2 slightly increases towards the center of the walls (see FIGS. 21 to 24) in order to be adapted to a corresponding depressed portion of the end plate of the vertebral body. The front wall 1 and the back wall 2 have preferably a plurality of apertures 6 which have a diamond shape in the embodiment shown. However, the shape of the apertures 6 can also be circular, oval-shaped or otherwise shaped.

Figure 2:
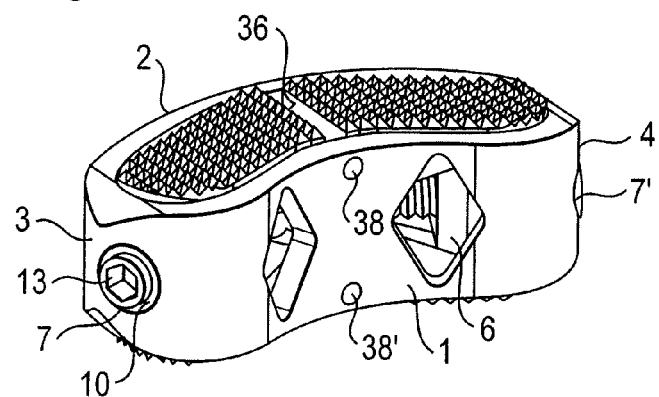
FIG. 2 shows a perspective front view of the assembled intervertebral implant of FIG. 1.

As shown in particular in FIGS. 1 and 2, the side walls 3 and 4 comprise bores 7, 7', respectively, at approximately their center. As can be seen best in FIG. 4 the bore 7 and the corresponding opposite bore 7' each have a first portion 8 with a first bore diameter adjacent to the outside of the side wall, respectively, and a following second portion 9 which opens into the cavity 5 and which has a second bore diameter which is slightly less than the first bore diameter. Thereby, the second portion 9 defines a shoulder.

A bearing member (or bearing journal) 10, 10', respectively is inserted into the bore 7, 7'. Each bearing member 10, 10' has a first cylindrical portion with a first outer diameter and adjacent thereto a second cylindrical portion with a second outer diameter matching the inner diameters of the first portion 8 and the second portion 9 of the bore 7, 7', so that the bearing member rests on the shoulder. The size of the bearing member 10, 10' is such, that the bearing member 10, 10' is held in the bore 7, 7', respectively, by press-fitting.

The implant further comprises two threaded spindles 11, 11', each having a first cylindrical end 12, 12' with a recess 13, 13', preferably a hexagon recess, at the free end for engagement with a tool (not shown). The outer diameter of the cylindrical first end 12, 12' is slightly smaller than the inner diameter of the bearing 10, 10' so that first end 12, 12' of the spindle can be inserted into the bearing 10, 10' and can be rotatably held therein. Each spindle further has a cylindrical second end 14, 14', opposite to the first end 12, 12'.

The thread pitches of the threaded spindles 11, 11' are opposite to each other. The length of the threaded spindles is such that when the spindles are held in the bearings 10, 10' and project into the cavity 5, the second ends 14, 14' of the spindles do not touch each other.

Figure 3:
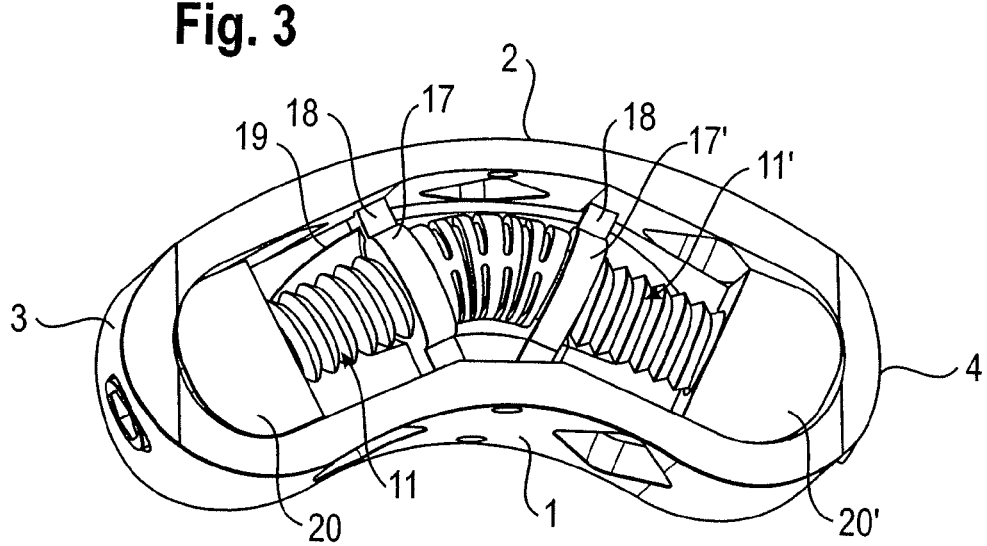
FIG. 3 shows a perspective top view of the intervertebral implant of FIGS. 1 and 2 with the upper engagement member omitted.
Figure 4:
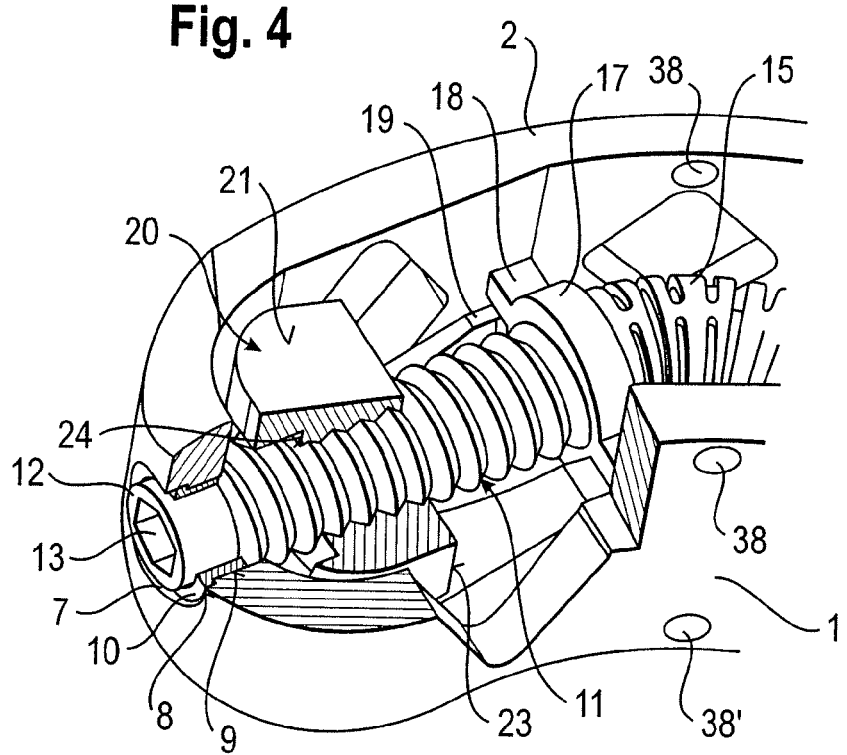
FIG. 4 shows a detail of FIG. 3 in an enlarged view, partly in section.
Figure 5:
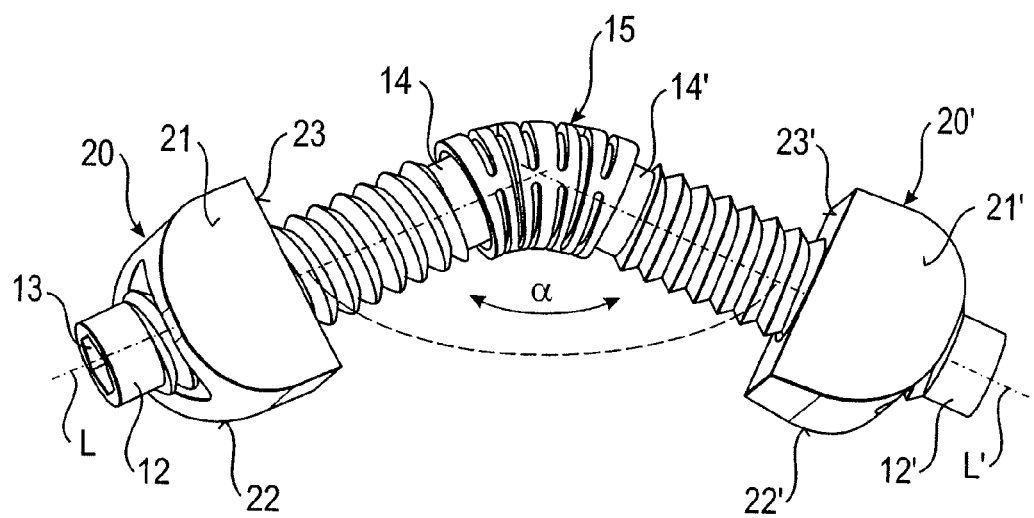
FIG. 5 shows the drive mechanism of the implant shown in FIG. 3.
Figure 6:
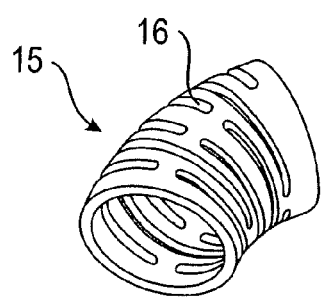
FIG. 6 shows a perspective front view of a coupling member of the coupling mechanism shown in FIG. 5.
Figure 7:
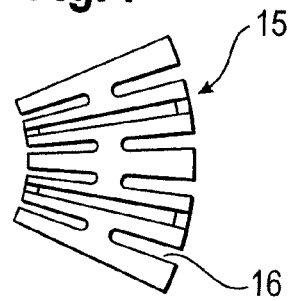
FIG. 7 shows a top view of the coupling member of FIG. 6.
Figure 8:
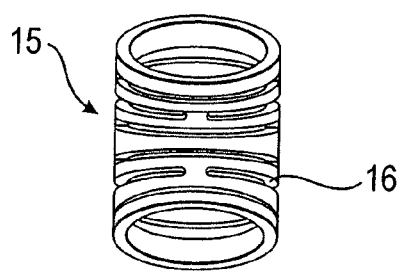
FIG. 8 shows a side view of the coupling member of FIG. 6.
Figure 9:
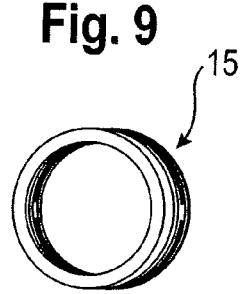
FIG. 9 shows another side view of the coupling member of FIG. 6.

As can be seen in particular in FIG. 3 to 5 the threaded spindles 11, 11' are connected with the second ends 14, 14' via a coupling member 15. The coupling member 15 in the embodiment shown in FIG. 1 to 7 is designed as a curved tube portion having slits 16 extending in a circumferential direction. The slits are offset from each other in such a way that the slits of one circumferential line cover at least such portions of an adjacent circumferential line, where no slit is provided. The inner diameter of the coupling member 15 is such that the coupling member 15 can be connected to the cylindrical end portions 14, 14' of the threaded spindles for example by means of a press-fit connection. The curvature and length of the coupling member is such that it is adapted to the angle α which the longitudinal axis L, L' of the threaded spindles 11, 11' enclose with each other. Accordingly, the curvature of the coupling member 15 corresponds substantially to the curvature of the front wall 1 and the back wall 2 of the implant. The number, width and length of the slits 16 are selected so as to provide a desired bending flexibility to the tube while providing sufficient torsional stiffness.

As can be seen in FIG. 3 a circular flange 17, 17' can be provided at the end 14, 14' of each spindle 11, 11' to provide a stop the function of which will be described later. The flange 17, 17' has a projection 18 on opposite sides which rests on a shoulder 19 provided at the inner side of the front wall 1 and the back wall 2, respectively. The flange 17, 17' also provides for a guidance and/or support for the spindles and the coupling member.

As can be seen in particular in FIGS. 1 and 3-5, a wedge member 20, 20' is provided on each threaded spindle 11, 11'. Each wedge member is defined by a top face 21, 21' and an opposite bottom face 22, 22' which include an angle with each other to define the wedge-shape. Each wedge member 20, 20' comprises a flat front wall 23, 23' and a curved rear wall and flat side walls. The flat front wall 23, 23' and the top wall 21, 21' and the bottom wall 22, 22' are arranged such that the distance increases between top wall and bottom wall in a direction away from the front wall. The wedge member 20, 20' comprises a threaded bore 24, 24' having an internal thread corresponding to the external thread of the threaded spindle 11, 11', respectively. The wedge members 20, 20' are screwed onto the corresponding threaded spindles 11, 11' in such a position that their corresponding top faces 21, 21' and bottom faces 22, 22' are inclined towards each other. As can be seen in particular in FIG. 3, the back walls of the wedge members are curved in such a way that they fit to the curvature of the inner side of the side walls 3, 4 of the implant.

As shown best in FIGS. 1, 2 and 15 to 18, a first engagement member 30 and a second engagement member 30', respectively, is placed between the mutually inclined top faces 21, 21' and mutually inclined bottom faces 22, 22', which will be referred to as wedge faces, of the wedge members 20, 20'. Each engagement member 30, 30' has on its lower face facing the wedge members two mutually inclined sloping surfaces 31, 32 and 31', 32', respectively. The angle of inclination of the surfaces 31, 32 and 31', 32', respectively, corresponds to the wedge angle of the wedge members. Between the left and right inclined surfaces 31, 32 and 31', 32', the engagement member 30, 30' comprises a substantially curved cylindrical recess 33, 33' which is sized so as to be able to accommodate the coupling member 15 including the flanges 17, 17'. The recess 33, 33' runs out into the inclined surfaces 31, 32 and 31', 32', respectively. The inclined surfaces of the engagement members 30, 30' and the wedge faces of the wedge members 20, 20' can slide onto each other. To enhance the sliding capability, the faces can be coated with a coating or can be polished.

Figure 16:
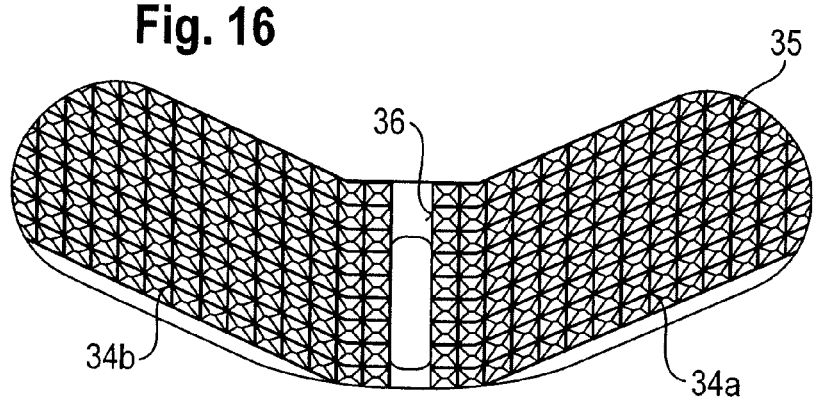
FIG. 16 shows a perspective top view of the engagement member of FIG. 15
Figure 17:
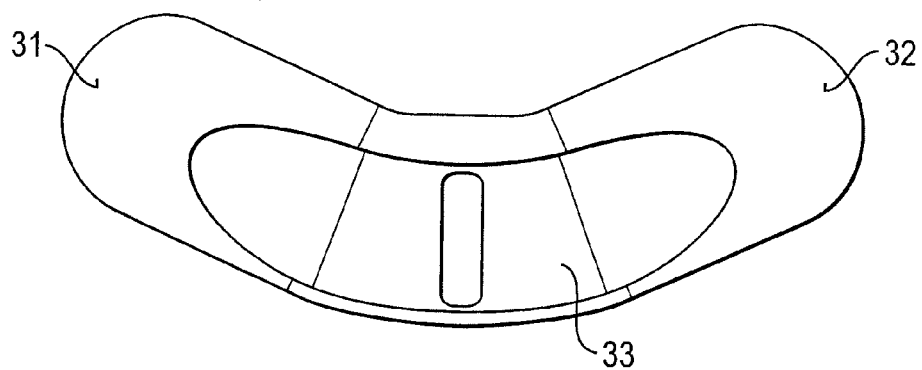
FIG. 17 shows a perspective bottom view of the engagement member of FIG. 15.
Figure 18:
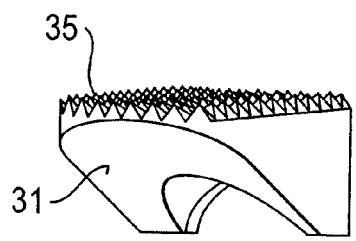
FIG. 18 shows a perspective view of an outer portion of the engagement member of FIG. 19 shows a side view of an engagement member of the implant according to a second embodiment.

As can be seen in particular in FIGS. 16 and 17, the contour of the engagement members is approximately banana-shaped or kidney-shaped and corresponds to the contour of the implant body as shown in FIGS. 1 and 2. The top surface 34 of the engagement member 30 has in the embodiment shown a right portion 34a and a left portion 34b which have a slight inclination with respect to each other, the inclination being opposite to the inclination of the inclined surfaces 31, 32 on the lower side. The second engagement member 31' has a corresponding top surface 34' with inclined portions 34a', 34b' (not shown). The top surface 34 further has an engagement structure 35 which can be designed as teeth projecting from the surface or as ribs or as any other structure which is suitable for engagement with the surface of the end plates of the vertebral body.

As can be seen in FIGS. 1, 2, 15 and 16, each engagement member 30, 30' comprises a substantially U-shaped slit 36, 36' extending from the top surface 34, 34' to a certain distance therefrom. The front wall 1 and the back wall 2 each comprise bores 38, 38' located in the center between the side walls, one in the upper half and one in the lower half. Two pins 39, 39' extend through opposite bores 38 across the cavity 5. The pins 39, 39' engage the U-shaped slits 36 of the engagement members 30, 30', respectively. By means of this, a stop is formed preventing falling-out of the engagement members 30, 30'. The U-shaped slits 36 also form a guidance for the engagement members 30, 30'.

The arrangement of the pins 39, 39' and the depth of the U-shaped slits 36, 36' are matched to each other such that the maximum heights of outward movement of the respective engagement members over the bottom face and the top face is determined by the relative position of the pin 39, 39' and the depth of the slits 36.

Figure 21:
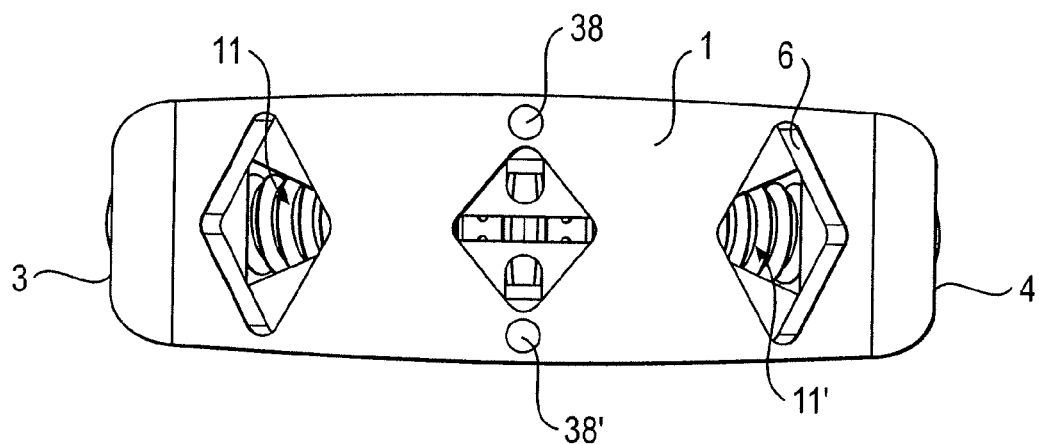
FIG. 21 shows a front view of the expandable intervertebral implant with the engagement members in a retracted position.
Figure 22:
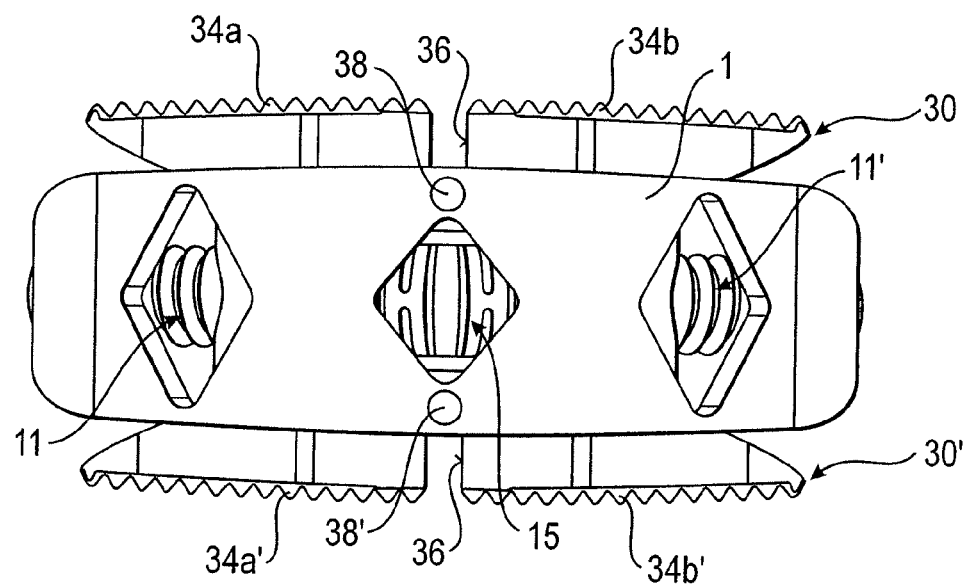
FIG. 22 shows a front view of the expandable intervertebral implant with the engagement members in an expanded position.
Figure 23:
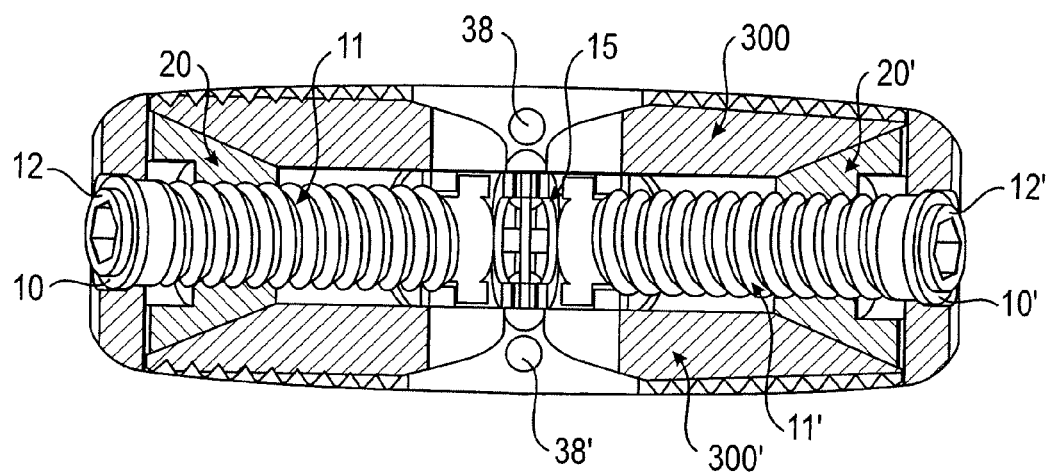
FIG. 23 shows an implant partially in section with the engagement members of FIG. 19 in the retracted condition.
Figure 24:
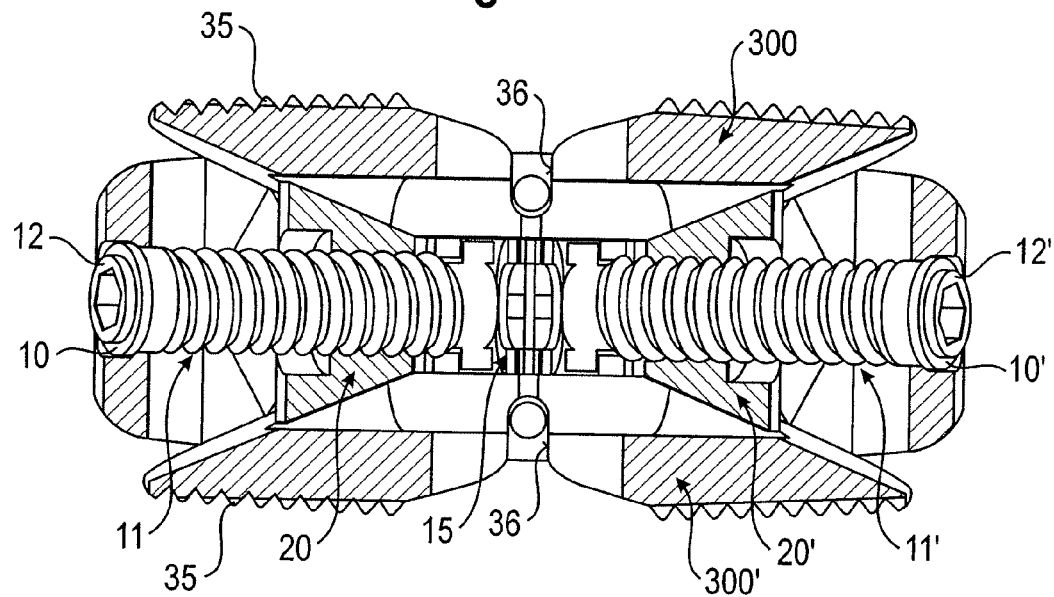
FIG. 24 shows an implant partially in section with the engagement members of FIG. 19 in the expanded position.

The dimensions of the wedge members 20, 20', the threaded spindles 11, 111' and the engagement members 30, 30' as well as the pitch of the threads is designed so as to allow the engagement members to be displaced from a first position shown in FIGS. 21 and 23 in which the top surface 34, 34' is located in the cavity 5 to a second position shown in FIGS. 22 and 24 in which the top surface 34, 34' projects above the cavity 5 of the implant.

The implant is manufactured from a biocompatible material, such as titanium, a biocompatible plastic material or other biocompatible materials. The coupling member 15 is for example manufactured from stainless steel or titanium to provide sufficient strength.

In operation, first, the wedge members 20, 20' are brought into the position shown in FIG. 3 wherein the back walls are in contact with the inner sides of the side walls 34 of the implant by rotating one of the threaded spindles. This causes each engagement member 30, 30' to take up its lowermost position wherein the engagement structure 35 of the top surface 34, 34' does not project beyond the cavity 5 of the implant. The implant can therefore easily be inserted into the area between two vertebrae and there is no risk of injuring the soft parts of the end plates of the vertebrae. Since the contour of the implant is approximately banana-shaped the insertion is facilitated compared to the insertion of a rectangular implant. The implant can be inserted in such a way that the front wall is oriented in the dorsal direction and the back wall is oriented in the ventral direction and the side walls are oriented laterally. The indication of the front, back and side wall does not limit the use of the implant to the particular way of insertion and is merely for the distinction of the walls with respect to each other. After having correctly positioned the implant between the vertebrae, the two wedge members 20, 20' are moved towards each other by engaging one of the threaded spindles 11, 11' by accessing it from one of the side walls 3, 4 with a tool, for example with an Allen wrench engaging the recess 13, 13' of the spindle. By rotating one of the threaded spindles the rotational movement is transferred by the coupling member 15 to the other threaded spindle. In the embodiment shown in FIGS. 1 to 7, the coupling member 15 has weakened portions at its slits 16 in order to provide a bending capability with sufficient torsional stiffness which allows to transfer the rotational motion of one spindle to the other spindle. By rotating one of the spindles the mutually inclined wedge surfaces 21, 22 and 21', 22' of the two opposed wedge members 20, 20' exert a force onto the inclined surfaces 31, 32 and 31', 32' of the corresponding engagement members 30, 30' to raise the same until the engagement structure 35 of the top surface 34, 34' projects out of the cavity 5 to thereby engage the end plates of the respective vertebrae. The lifting movement of the engagement members 30, 30' is limited by the stop formed by the pins 39, 39' as particularly shown in FIG. 24. The flanges 17, 17' can also provide a stop for the movement of the wedge members.

The transmission of the rotation of the tool through one threaded spindle to the other threaded spindle and from the wedge members to the engagement members allows a precise adjustment of the expansion of the engagement members and allows for an individual adaptation of the implant to the anatomical shape of the end plates of the vertebrae of the individual patient.

The threaded spindles prevent the engagement members from becoming loose by themselves. The engagement members 30, 30' can be retracted only by backward rotation using a tool whereby the pressure exerted by the vertebrae onto the engagement members forces the engagement members back into the cavity 5 of the implant. This releases the engagement structure from the end plates of the vertebrae.

Figure 19:
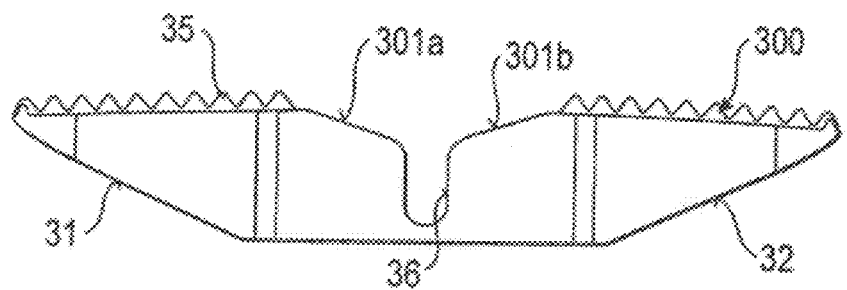
Figure 20:
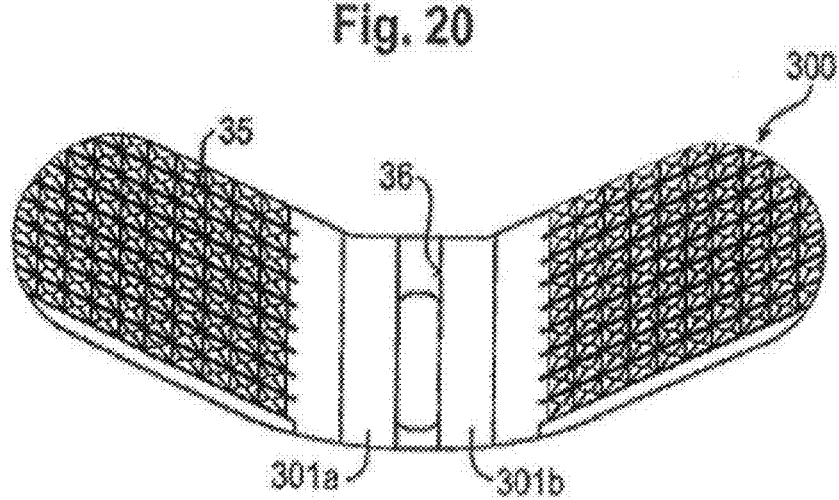
FIG. 20 shows a perspective top view of the engagement member of FIG. 19.

FIGS. 19 and 20 show an alternative embodiment of the engagement member. The engagement member 300 differs from the engagement member 30, 30' in that it has two opposed slanted surfaces 301a, 301b adjacent to the U-shaped recess 36 the inclination of which can be parallel to the inclination of the inclined surfaces 31, 32 on the lower side of the engagement member 300. The slanted surfaces 301a, 301b do not have an engagement structure. By means of the engagement members 300 of this embodiment, support is provided at the outer part of the end-plate, where the highest bone strength is provided.

Figure 10:
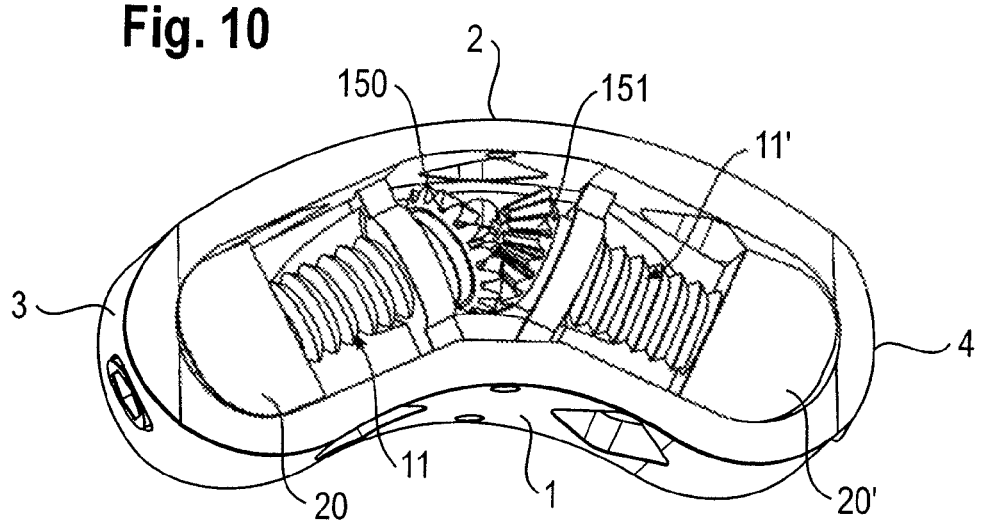
FIG. 10 shows a perspective view of the implant according to FIGS. 1 and 2 with a d coupling mechanism and the upper engagement member being omitted.
Figure 11:
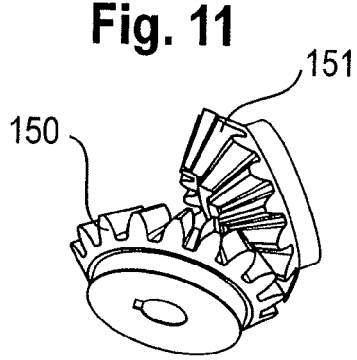
FIG. 11 shows a detail of the modified coupling mechanism.
Figure 12:
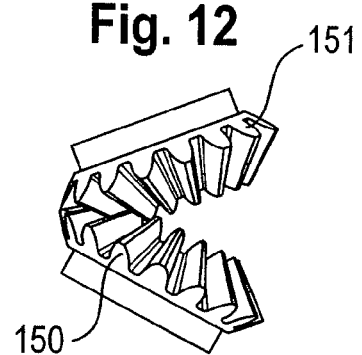
FIG. 12 shows a side view of the coupling mechanism shown in FIG. 11.

A further modification of the coupling mechanism to transfer the rotational movement from one spindle to the other spindle is shown in FIGS. 10 to 12. The coupling mechanism can be formed by a bevel gear drive comprising two pinions 150, 151 engaging each other. Each pinion is non-rotatably connected to the spindles 11, 11'.

Figure 13:
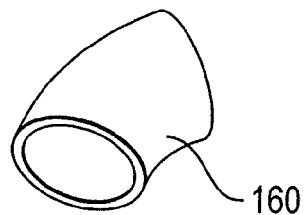
FIG. 13 shows a perspective top view of another modified coupling mechanism.
Figure 14:
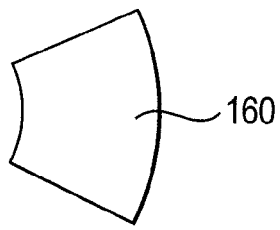
FIG. 14 shows a top view of the member of FIG. 13.

A further modified embodiment of the coupling mechanism for transferring the rotational movement of one spindle to the other spindle is shown in FIGS. 13 and 14. The coupling mechanism includes a flexible tube 160 which has a curvature and dimensions similar to the coupling member 15 shown in FIGS. 1 to 7 and which is sized so as to be press-fit connected to the ends 14, 14' of the spindles. The coupling member 160 transfers the rotational movement by a deformation of the flexible material. The coupling member 160 can be made for example, from nitinol or flexible plastic material with bending flexibility but torsional stiffness.

Figure 25B:
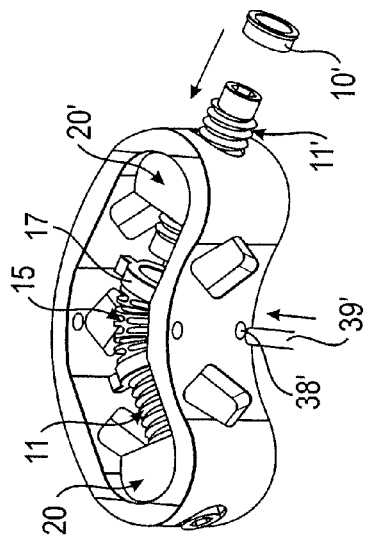
FIG. 25a to 25e show steps of assembling the intervertebral implant.
Figure 25E:
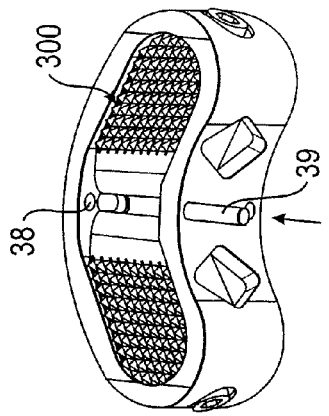
Figure 25A:
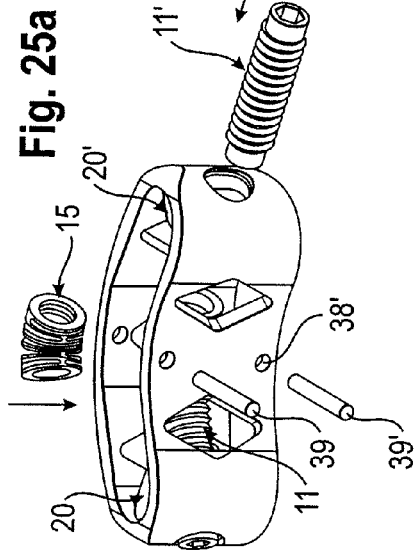
Figure 25D:
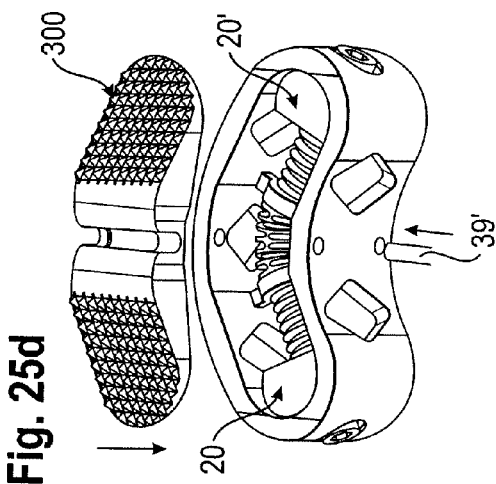
Figure 25C:
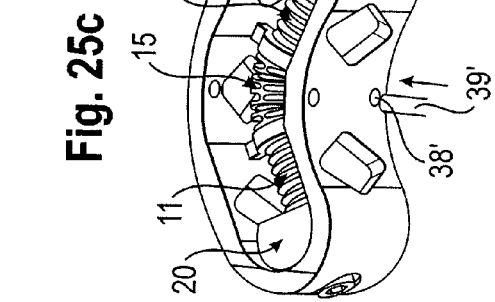

FIGS. 25a to 25e show steps for assembly of the implant. In the first step shown in FIG. 25a, the first spindle with the corresponding wedge-member screwed thereon is inserted into the cavity and the corresponding bearing. As a next step the coupling member 15 is connected to the first spindle. Then, the second wedge member is inserted, the second spindle guided through the second bore and screwed through the second wedge member until it can be connected with the flange of the coupling member. Then, the second bearing is inserted (FIGS. 25a and 25b). As shown in FIGS. 25c and 25d, when the spindles including the wedge members are inserted and coupled by the coupling member the engagement members can be inserted and the pins 39, 39' put through the bores 38, 38', as shown in FIG. 25e.

Although the walls are described as front wall, back wall and side walls, this is not to be understood as a limitation for the orientation of the implant between the vertebrae. The shape of the implant is not restricted to a banana shape or kidney shape. For example, the shape can be ring-shaped or a quarter ring or a half ring or any other shape.

It is also conceivable that more than two wedge members on more than two supporting members are provided enclosing an angle with each other. For example three support spindles enclosing an angle of 120° with each other and three adjustment or wedge members can be provided.

Other coupling mechanisms are conceivable, for example a corrugated tube, a cardan joint or a bowden cable. Even non mechanical couplings, for example, a magnetic coupling is possible.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. An expandable intervertebral implant comprising:
   a front wall;
   a back wall spaced apart from the front wall;
   two side walls connecting the front wall and the back wall at their respective ends, the front wall, back wall and the two side walls defining a space;
   a bottom face;
   a top face;
   at least one engagement member with an engagement surface configured to engage an end plate of a vertebral body;
   a first adjusting element configured to contact a first portion of the engagement member and a second adjusting element configured to contact a second portion of the engagement member, which are supported by and translationally moveable relative to a first support member and a second support member, respectively, and which cooperate with the respective support member such that the engagement member is reciprocally movable between a first end position and a second end position wherein the engagement surface at least partially projects outwardly beyond the bottom face or the top face, the second end position being different from the first end position;
   wherein the first and the second support members are coupled by a coupling mechanism; and
   wherein an axis of movement of the first support member and an axis of movement of the second support member define an angle which is different from zero.

2. The intervertebral implant of claim 1, wherein the coupling mechanism transfers the rotation of the first support member to the second support member.

3. The intervertebral implant of claim 1, wherein the coupling mechanism comprises a rotational coupling.

4. The intervertebral implant of claim 1, wherein the coupling mechanism comprises a flexible tube.

5. The intervertebral implant of claim 1, wherein the coupling mechanism comprises one of a bevel gear drive, a tube made of rigid material with bending zones and a flexible tube drive.

6. The intervertebral implant of claim 1, wherein the support members are formed as first and second threaded spindles having opposite thread pitch.

7. The intervertebral implant of claim 1, wherein the adjusting elements are wedge members, said wedge members operating to move the engagement member.

8. The intervertebral implant according to claim 6, wherein the adjusting elements are formed as wedge members and one end of the first threaded spindle being rotationally supported in the first side wall, one end of the second threaded spindle being rotationally supported in the second side wall and the other ends being rotationally coupled to each other; and
   wherein the two wedge members are supported within the space in such a manner, that, upon rotation of the first or the second threaded spindle in one direction a distance between the wedge members decreases and upon rotation of the threaded spindle in an opposite direction the distance between the wedge members increases, and said wedge members operate to move the engagement element.

9. The intervertebral implant according to claim 6, wherein the engagement member has two inclined surfaces on a side opposite to said engagement surface and wherein the wedge members engage the inclined surfaces.

10. The intervertebral implant according to claim 1, wherein at least the front wall or the back wall is curved.

11. The intervertebral implant according to claim 1, wherein the front and back walls of the implant are curved in such a way that the contour of the space which is formed by the walls is bent substantially at an angle corresponding to the angle defined by the axes of movement of the first and second support members.

12. The intervertebral implant according to claim 1, wherein the engagement surface of the engagement member comprises an engagement structure for penetration into an adjacent bone material.

13. An intervertebral implant according to claim 1, further comprising a stop that limits the outward movement of the engagement member.

14. The intervertebral implant according to claim 1, comprising two engagement members movable in opposite directions.

15. The intervertebral implant according to claim 1, wherein the first support member and the second support member are each supported in one of said walls.

16. The intervertebral implant according to claim 1, wherein the adjusting elements are each guided by two of the walls.

17. The intervertebral implant according to claim 7, wherein the engagement member has two inclined surfaces on a side opposite to said engagement surface and wherein the wedge members engage the inclined surfaces.

18. The intervertebral implant according to claim 1, wherein the first support member is rotatable about the axis of movement of the first support member and the second support member is rotatable about the axis of movement of the second support member.

19. A method of replacing an intervertebral disk with an expandable intervertebral implant comprising a front wall, a back wall spaced apart from the front wall, two side walls connecting the front wall and the back wall at their respective ends, the front wall, back wall and the two side walls defining a space, the implant further comprising a bottom face, a top face, at least one engagement member with an engagement surface configured to engage an end plate of a vertebral body, a first adjusting element configured to contact a first portion of the engagement member and a second adjusting element configured to contact a second portion of the engagement member, which are supported by and translationally moveable relative to a first support member and a second support member, respectively, and which cooperate with the respective support member such that the engagement member is reciprocally movable between a first end position and a second end position wherein the engagement surface at least partially projects outwardly beyond the bottom face or the top face, the second end position being different from the first end position, wherein the first and the second support members are coupled by a coupling mechanism, and wherein an axis of movement of the first support member and an axis of movement of the second support member define an angle which is different from zero, the method comprising:

inserting the intervertebral implant between two vertebral bodies; and moving the at least one engagement member from the first end position to an implanted position between the first end position and the second end position;

wherein the engagement surface of the at least one engagement member engages the end plate of one of the vertebral bodies in the implanted position of the engagement member.

20. The method of claim 19, where moving the at least one engagement member comprises rotating the first support member about the axis of movement of the first support member and rotating the second support member about the axis of movement of the second support member.

* * * * *

UNITED STATES PATENT AND TRADEMARK OFFICE
CERTIFICATE OF CORRECTION

| | | |
|---|---|---|
| PATENT NO. | : 8,366,777 B2 | |
| APPLICATION NO. | : 11/944580 | |
| DATED | : February 5, 2013 | |
| INVENTOR(S) | : Wilfried Mathis et al. | |

It is certified that error appears in the above-identified patent and that said Letters Patent is hereby corrected as shown below:

In the Specification

Column 2, line 47      Delete "d"
Insert -- modified --

Figure 15:
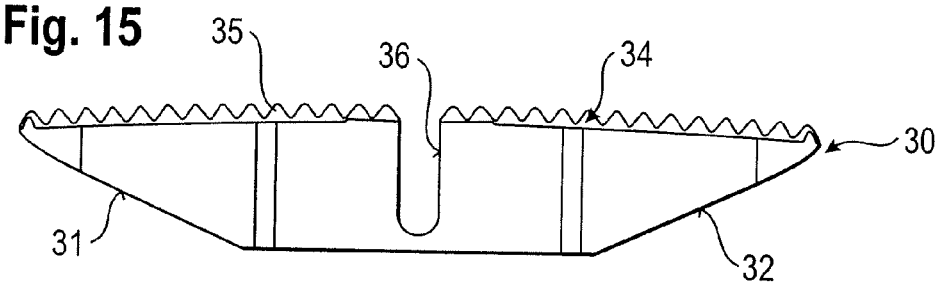
FIG. 15 shows a side view of an engagement member of the implant in a first embodiment.

Column 2, line 63      After "of"
Insert -- FIG. 15. --

Column 5, line 40      Delete "11, 111'"
Insert -- 11, 11' --

Signed and Sealed this
Fourth Day of March, 2014

Michelle K. Lee
*Deputy Director of the United States Patent and Trademark Office*